(12) United States Patent
Ding

(10) Patent No.: US 7,755,376 B2
(45) Date of Patent: Jul. 13, 2010

(54) CAMERA BASED PIN GRID ARRAY (PGA) INSPECTION SYSTEM WITH PIN BASE MASK AND LOW ANGLE LIGHTING

(75) Inventor: Kexiang Ken Ding, San Diego, CA (US)

(73) Assignee: Delta Design, Inc., Poway, CA (US)

( * ) Notice: Subject to any disclaimer, the term of this patent is extended or adjusted under 35 U.S.C. 154(b) by 445 days.

(21) Appl. No.: 11/545,460

(22) Filed: Oct. 11, 2006

(65) Prior Publication Data

US 2007/0080703 A1 Apr. 12, 2007

Related U.S. Application Data

(60) Provisional application No. 60/725,296, filed on Oct. 12, 2005.

(51) Int. Cl.
*G01R 31/02* (2006.01)
(52) U.S. Cl. ...................................... 324/758
(58) Field of Classification Search ................. 324/765, 324/158.1, 750–751, 758; 356/614, 399; 257/48
See application file for complete search history.

(56) References Cited

U.S. PATENT DOCUMENTS

| 4,728,195 A | 3/1988 | Silver |
| 5,440,391 A | 8/1995 | Smeyers et al. |
| 5,648,853 A | 7/1997 | Stern et al. |
| 6,388,457 B1 * | 5/2002 | Loh et al. .................... 324/755 |
| 6,489,790 B1 * | 12/2002 | An et al. ...................... 324/755 |
| 7,193,728 B2 * | 3/2007 | Ichikawa et al. ............ 356/614 |
| 2007/0023716 A1 | 2/2007 | van der Burgt et al. |

FOREIGN PATENT DOCUMENTS

| EP | 1 065 499 A2 | 1/2001 |
| EP | 1 079 420 A2 | 2/2001 |
| JP | 8-68615 | 3/1996 |
| TW | 533999 | 5/2003 |

\* cited by examiner

*Primary Examiner*—Ha Tran T Nguyen
*Assistant Examiner*—Tung X Nguyen
(74) *Attorney, Agent, or Firm*—Foley & Lardner LLP

(57) ABSTRACT

An inspection system, for inspecting pin grid arrays on integrated circuit devices includes a pin base mask configured to receive a device having a pin grid array. A dark-field, low-angle lighting system emits light onto the pin grid array. The pin base mask and low-angle lighting system provide for a clear and definitive image of the pin grid array. A camera captures the image of the pin grid array. A processor, coupled to the camera, analyzes the images captured by the camera. Based on the captured image, the processor determines whether any pins on the pin grid array are bent or missing, or whether there are extra pins present.

24 Claims, 9 Drawing Sheets

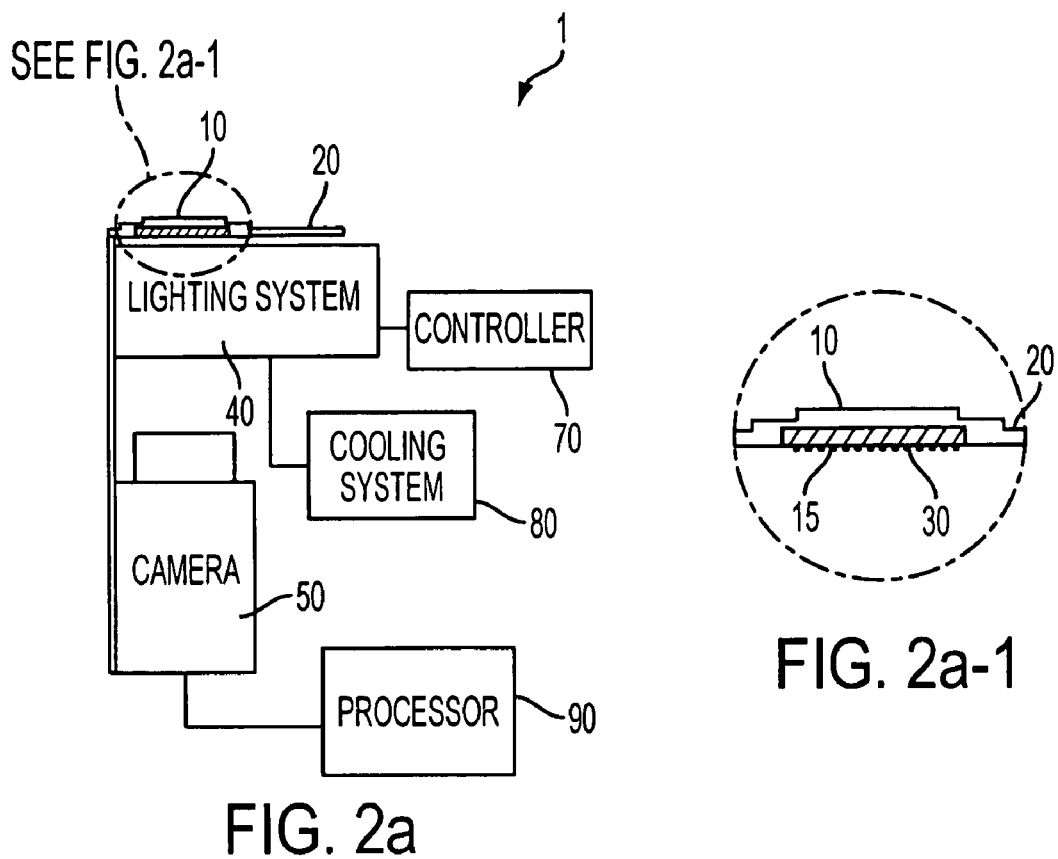
FIG. 2a
FIG. 2a-1
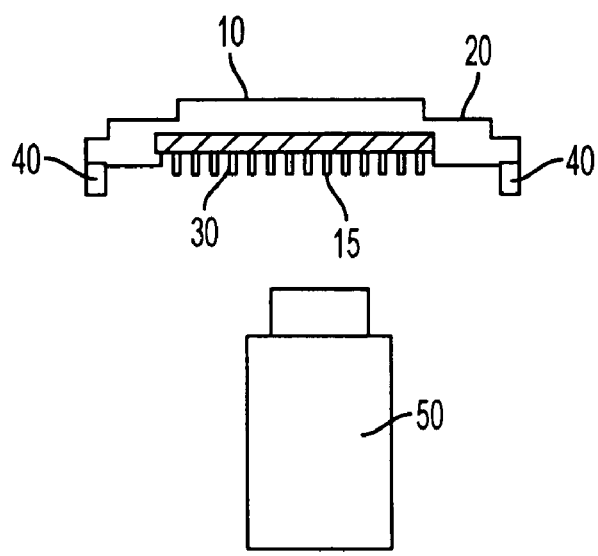
FIG. 2b

CAMERA BASED PIN GRID ARRAY (PGA) INSPECTION SYSTEM WITH PIN BASE MASK AND LOW ANGLE LIGHTING

CROSS-REFERENCE TO RELATED PATENT APPLICATIONS

This application claims priority from Provisional U.S. Application No. 60/725,296, filed Oct. 12, 2005, incorporated herein by reference in its entirety.

FIELD OF INVENTION

The present invention relates generally to a device inspection system, and more particularly to a camera-implemented pin grid array ("PGA") inspection system.

BACKGROUND OF THE INVENTION

Manufacturers process and test semiconductor or integrated circuit ("IC") devices using various types of automated machinery. Before IC devices are shipped to wholesalers or consumers, they must be tested for performance and inspected for physical defects. One physical defect that is important to identify is the presence of bent pins on IC devices having a pin grid array ("PGA").

Generally, mechanical systems or basic camera systems are employed to identify bent pins. However, current mechanical and camera systems are limited in their ability to detect bent pins accurately. Conventional mechanical systems lack the ability to provide information beyond simply identifying bent pins. In addition, basic vision systems that use cameras to detect bent pins are limited in their effectiveness because generally, the contrast between a tip of a pin and the pin base is poor. The poor contrast between a tip of a pin and the pin base also prevents basic vision systems from accurately detecting bent pins on a pin grid array.

Other conventional systems have operational drawbacks as well. For example, one conventional camera system uses a generic lighting system in conjunction with blob analysis. In a binary image, a blob is an area of pixels with the same logical state. Blob analysis is used to detect and make measurements of blobs in an image. However, the lighting used in blob analysis systems is not uniform, which results in less than reliable detection results. Yet another known inspection system implements 3D detection on a PGA. However, due to the complexity needed to obtain a three-dimensional image, this method is unnecessarily expensive and therefore an undesirable option.

Therefore, it would be desirable to provide an inexpensive system that is capable of accurately detecting bent pins on a PGA and providing detailed information about individual pins in a PGA.

SUMMARY OF THE INVENTION

According to one embodiment of the invention, an inspection system includes a pin base mask having a plurality of pin holes configured to receive a plurality of pins on a pin grid array of a device to be inspected, a dark-field, low-angle lighting system for illuminating the pins on the pin grid array, wherein the dark-field, low-angle lighting system is positioned in proximity to the pin base mask, a camera configured to image the illuminated pins of the device and a processor coupled to the camera, configured to analyze images captured by the camera to detect defects in the pin grid array.

According to another embodiment of the invention, a method for inspecting a pin grid array of a device in a test handler, includes the steps of applying a pin base mask to a substrate of the device, illuminating the surface of the pin grid array with dark-field, low-angle light at an angle of approximately zero degrees relative to the surface of the pin grid array, inspecting the pin grid array based on a predetermined trained model and if a pin defect is detected, removing the device from the test handler for repair.

According to yet another embodiment of the invention, a system for inspecting a pin grid array of a device in a test handler, includes means for applying a pin base mask to a substrate of the device, means for illuminating the surface of the pin grid array with dark-field, low-angle light at an angle of approximately zero degrees relative to the surface of the pin grid array, means for inspecting the pin grid array based on a predetermined trained model and if a pin defect is detected, means for removing the device from the test handler for repair.

According to still another embodiment of the invention, A test handler for inspecting an integrated circuit device, includes a pin grid array inspection system, having a pin base mask and a dark-field, low-angle lighting system, an alignment detection system, an electrical testing system, an identification detection system; and a pick and place handler and a multiple arm turret assembly for transporting the integrated circuit device through the test handler. Other features and advantages of the invention will be apparent from the following description.

BRIEF DESCRIPTION OF THE DRAWINGS

FIG. 2(a) is a block diagram of a PGA inspection system according to an embodiment of the invention.

FIG. 2(b) is a block diagram of a camera and a dark-field low-angle lighting system projecting low-angle light onto an IC device in accordance with an embodiment of the invention.

DETAILED DESCRIPTION OF THE PREFERRED EMBODIMENTS

Figure 1:
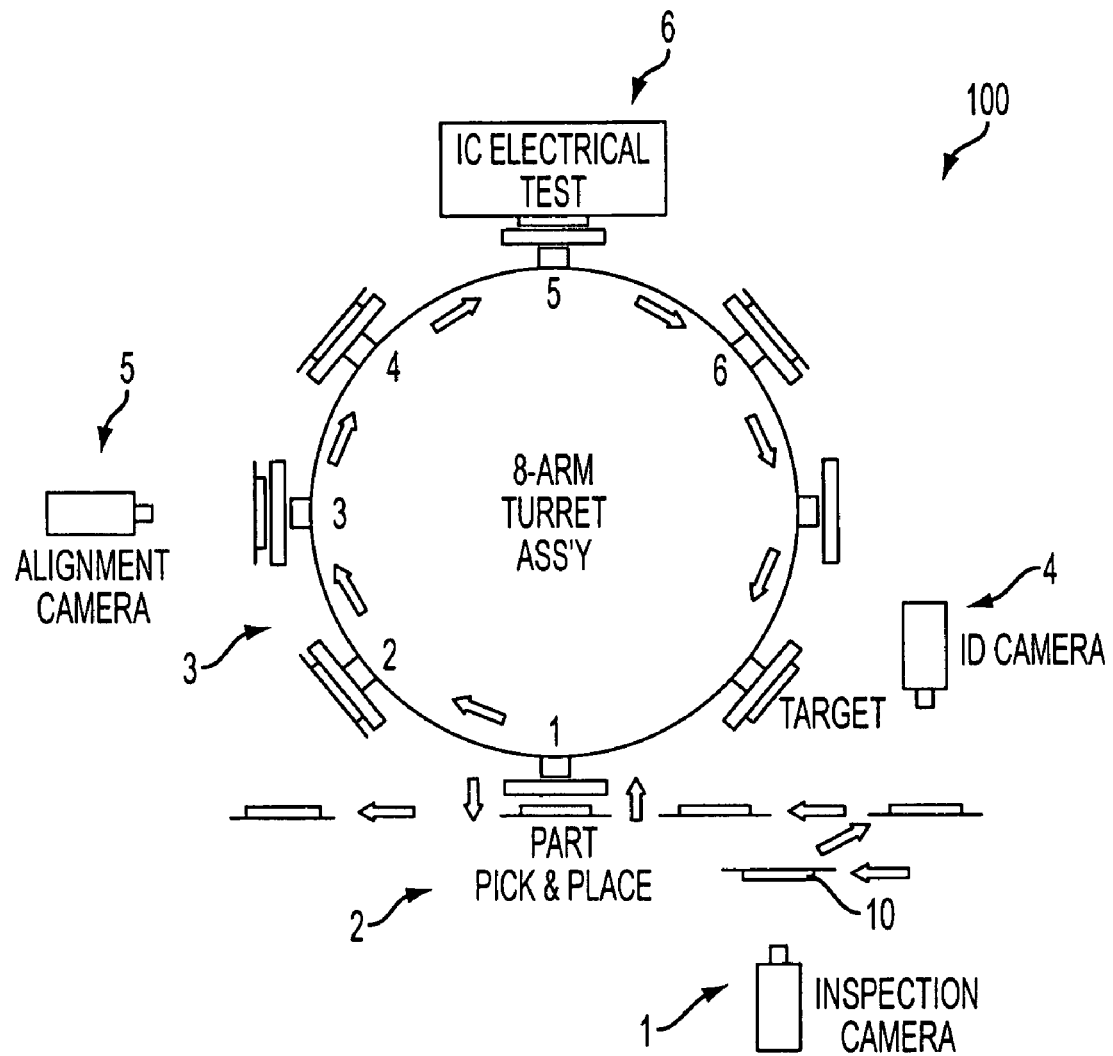
FIG. 1 is a schematic of a workflow for an IC device inspection system according to an embodiment of the invention.

Generally, IC inspection systems carry out a number of individual tests on each IC device during and after the manufacturing process. FIG. 1 depicts the workflow of one illustrative IC inspection system 100 in which the invention may be incorporated. It will be appreciated that the invention may be used in other inspection systems. In this example, the IC device 10 is inspected at various stations throughout the IC inspection system 100. The IC device 10 is moved through the IC inspection system 100 on a carrier via a part handler. The part handler of this example may consist of a pick and place handler 2 and a multiple-arm turret assembly 3. A pick and place handler 2 and turret assembly 3 are used to move and position IC devices 10 during various manufacturing phases.

In this particular example, several inspection steps, using different systems are employed to test each IC device 10. As shown in FIG. 1, three inspection stations use vision systems. The physical defect inspection station 1 detects physical defects on the IC device 10. The identification vision system 4 aids in the identification of an IC device 10. Generally, a code is used to uniquely identify each specific IC device 10. The alignment vision system 5 determines the alignment of an IC device 10 as well as offset position information. All information captured by the vision systems 1,4,5 is processed by a microprocessor (not shown) running software for processing visual images captured during IC device 10 inspection. Finally, as shown in FIG. 1, the IC inspection system 100 may also include an electrical testing system 6 for conducting electrical tests on the IC device 10.

The physical defect inspection system 1, shown in FIG. 1, may be configured differently based on the type of IC device 10 under inspection. In the inspection of IC devices having a pin grid array, a PGA inspection system 1, described in detail below, may be used. According to one embodiment of the invention, if the PGA inspection system 1 detects physical defects on the subject IC device 10, such as a bent pin, the IC device 10 is removed via the pick and place handler 2 before it is inspected further. An exemplary PGA inspection system 1, according to the present invention, is now described in reference to the accompanying drawings. Of course, other applications may be apparent to those skilled in the art.

According to one embodiment of the invention, a PGA inspection system 1 is shown in FIG. 2(a). The PGA inspection system 1 is configured to inspect IC devices 10 having various sizes. For example, the IC devices 10 may have surface areas ranging from 25 mm×25 mm to 51 mm×51 mm. As shown in FIG. 2(a), an IC device 10, having a pin grid array 15, is positioned in a carrier 20.

Figure 3:
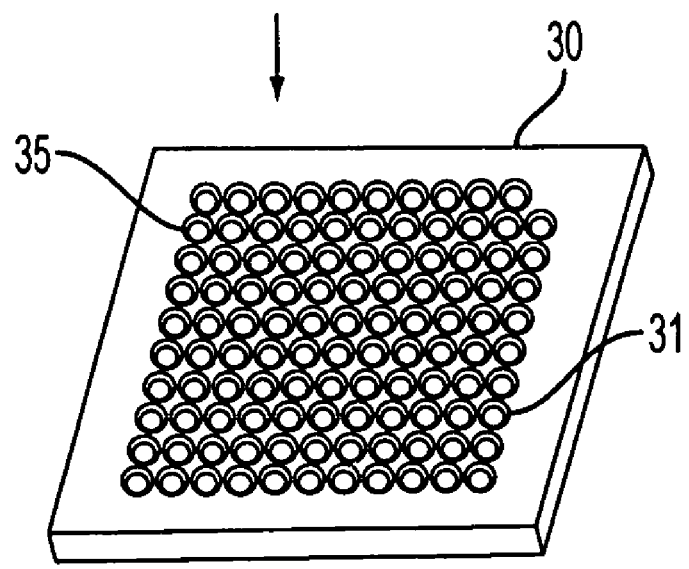
FIG. 3 is a perspective view of a pin base mask as used in an embodiment of the invention.
Figure 4A:
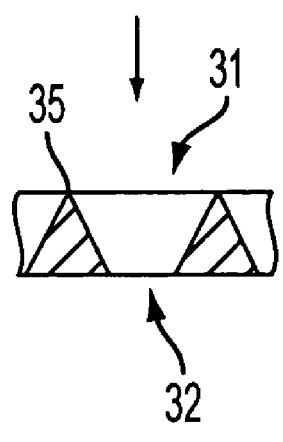
FIG. 4(a) is a section view of a pinhole on a pin base mask as used in an embodiment of the invention.
Figure 4B:
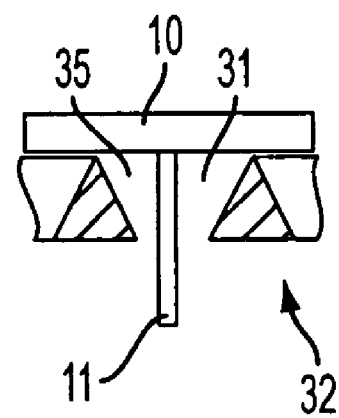
FIG. 4(b) is a section view of a pin inserted into the pinhole of a pin base mask as used in an embodiment of the invention.

A pin base mask 30, having a plurality of pin holes 35 is configured to complement the pin grid array 15 of the IC device 10 and receives the IC device 10 as shown in FIGS. 2(a) and 2(b). FIG. 3 shows a perspective view of a pin base mask 30 according to one embodiment of the invention. The pin base mask 30 has an input side 31 and an output side 32. The input side 31 of the pin hole 35 is larger than the output side 32. The larger input side 31 aids insertion of the pins into the pin base mask 30. As shown in FIGS. 4(a) and 4(b), each pin hole 35 of the pin base mask 30 is chamfered to guide the pins of the pin grid array 15 into the corresponding pin holes 35. In addition, the pin base mask 30 is preferably black on the pin output side 32 (facing the camera 50) and has a flat in surface. FIG. 4(b) is an enlarged view of a pin positioned within the pin hole 35 of a pin base mask 30. Thus, as shown, the pin base mask 30 is configured so that it effectively masks the pin bases 12 from the pin tips 11 of the IC device 10.

As shown in FIG. 2(b), according to one embodiment of the invention, a dark-field low-angle lighting system 40 is positioned below the IC device 10. FIG. 2(b) is a cross sectional depiction of the PGA system 1 for illustration purposes. It should be understood that the lighting system 40 may also include lighting elements positioned below the front and back sides of the mask 30. According to one embodiment of the invention, the dark-field, low angle lighting system is mounted to the pin base mask 30. The dark-field low-angle lighting system 40 is configured to provide uniform low-angle illumination onto the PGA 15 of the IC device 10. Dark-field illumination is generally used on reflective surfaces to create stark contrast between the background of the target and specific features. According to one embodiment of the invention, the angle of the dark-field light projected onto the PGA 15 of the IC device 10 is about 0° relative to the surface of the PGA 15. Preferably, the angle of the light emitted by the dark-field, low-angle lighting system is less than 10°. Thus, the angle of the light emitted by the dark field, low-angle lighting system relative to the surface of the PGA 15 can be in the in the range of 0° to 10°. The low-angle lighting creates shadows on the pin bases 12 so that when the pin base mask 30 is applied, only the pin tips 11 are highlighted, as illustrated, for example, in FIG. 6(a).

Figure 5:
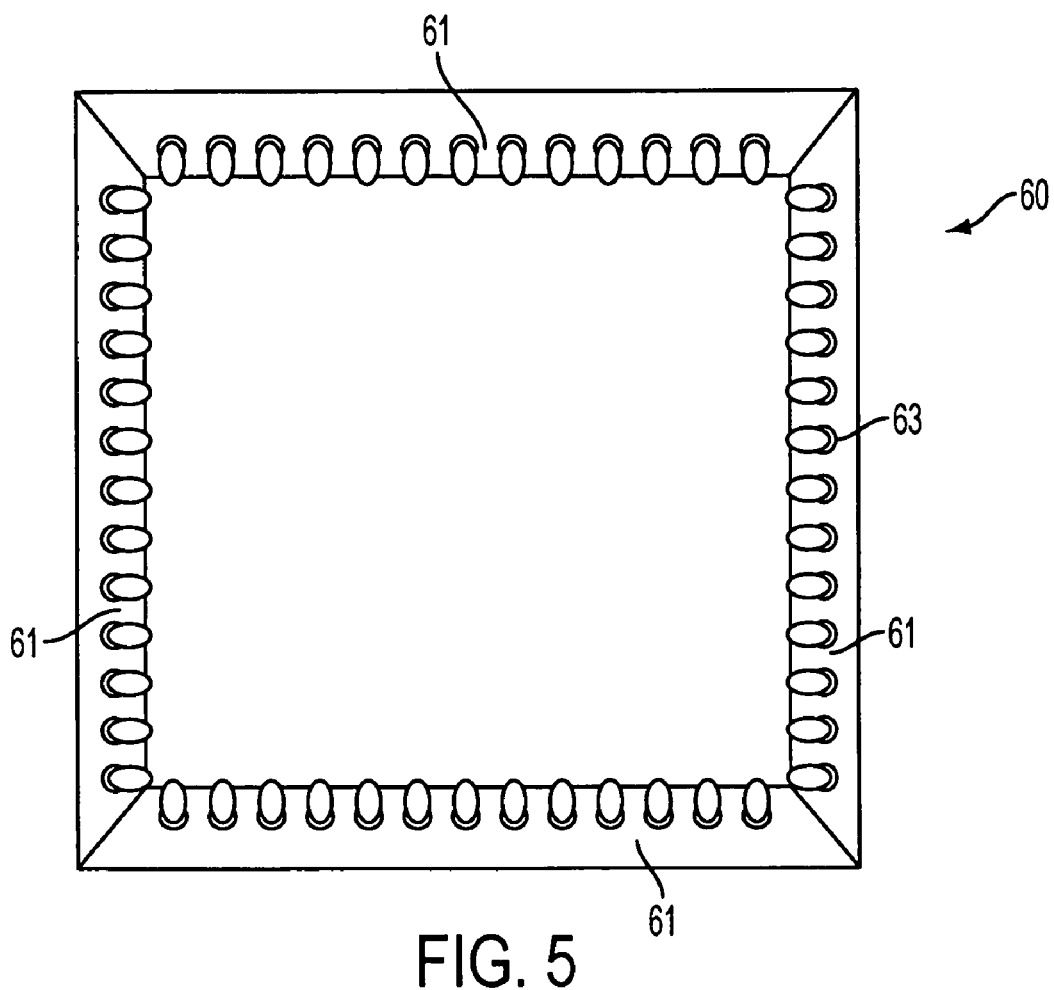
FIG. 5 is a block diagram of a light housing assembly as used in an embodiment of the invention.

FIG. 5 is a top view of a light housing assembly 60 for the dark-field low-angle lighting system 40 according to one embodiment of the invention. According to this embodiment, the dark-field low-angle lighting system 40 is comprised of four LED array bars 61 configured to surround the tops and sides of the pin tips that extend through the mask 30. According to another embodiment of the invention, LEDs with different characteristics may be used. The LEDs may also have various levels of intensity. For example, the LEDs may have a maximum intensity of 8300 mcd.

In an alternative embodiment, the light housing 60 may also contain mid-angle lighting and high-angle lighting in addition to the dark-field, low-angle lighting. The low-angle surface mounted LEDs 63, provided in this example, adjacent to the perimeter of the light housing assembly 60, provide dark-field low-angle lighting at an angle of about 0° relative to the surface of the PGA 15. As mentioned above, when a pin base mask 30 is applied to the PGA 15 and the PGA 15 is exposed to dark-field low-angle lighting, a stark contrast is created on the surface of the PGA 15. Each pin tip 11 of the PGA 15 is clearly distinguishable. This clearly distinguishable image is then captured by the camera 50 for image processing.

As illustrated in FIGS. 2(a) and 2(b), a camera 50 is positioned in the proximity of the dark-field low-angle lighting system 40 in order to obtain images of the pin grid array 15. Preferably, the camera is positioned so that its optical axis is approximately perpendicular to the surface of the pin grid array being illuminated. Preferably, the camera 50 is a megapixel camera. For example, according to one embodiment of the invention, a PULNiX® TM-1400 camera can be employed. The PULNiX® TM-1400 possesses an area imager with 1300×1000 active pixels. Further, according to one embodiment of the invention, in order to obtain optimum images of the IC device 10, the camera 50 has a focal length of 12 mm with its f/stop being set to eight.

In order for the camera 50 to obtain the best image, the pick and place handler 2 should accurately position the IC device 10 in the field of view of the camera 50. For example, according to one embodiment of the invention, the field of view of the camera 50 for large size IC devices 10 is approximately 71.5 mm×55 mm. Positional accuracy within predetermined ranges is desirable for placement within the field of view of the camera 50. For example, the tilt and rotational accuracy of the placement of the IC device 10 by the handler should preferably be within ±1°. The translational placement accuracy of the handler is preferably ±0.5 mm. Finally, according to one embodiment of the invention, the height placement accuracy of the handler is ±1 mm.

Figures 6A, 6B:
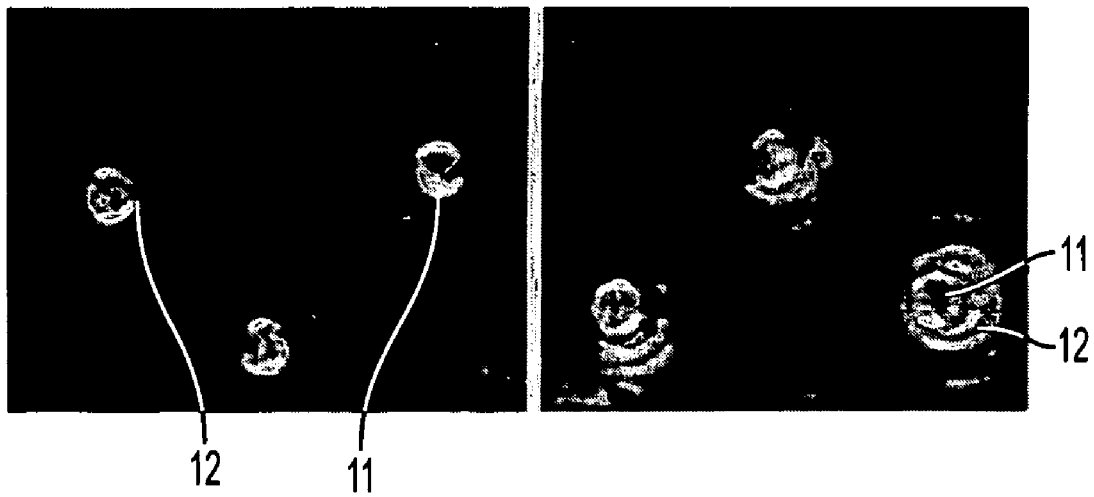
FIGS. 6(a)-6(b) show images of a pin tip and pin base viewed with a pin base mask and a pin tip and pin base viewed without a pin base mask, respectively.

FIGS. 6(a) and 6(b) illustrate the advantages provided by use of a mask. FIG. 6(a) is an image of a masked pin grid array. FIG. 6(b) shows an image of a PGA taken without a pin base mask 30. As shown in FIG. 6(b), the image obtained without a pin base mask provided on the pin grid array is less clear than FIG. 6(a). As shown, in FIG. 6(b), it is difficult to discern the pin tip 11 from the pin base 12. Accordingly, analyzing such an unclear image with an image processing algorithm may lead to less than accurate detection results.

Figure 7A:
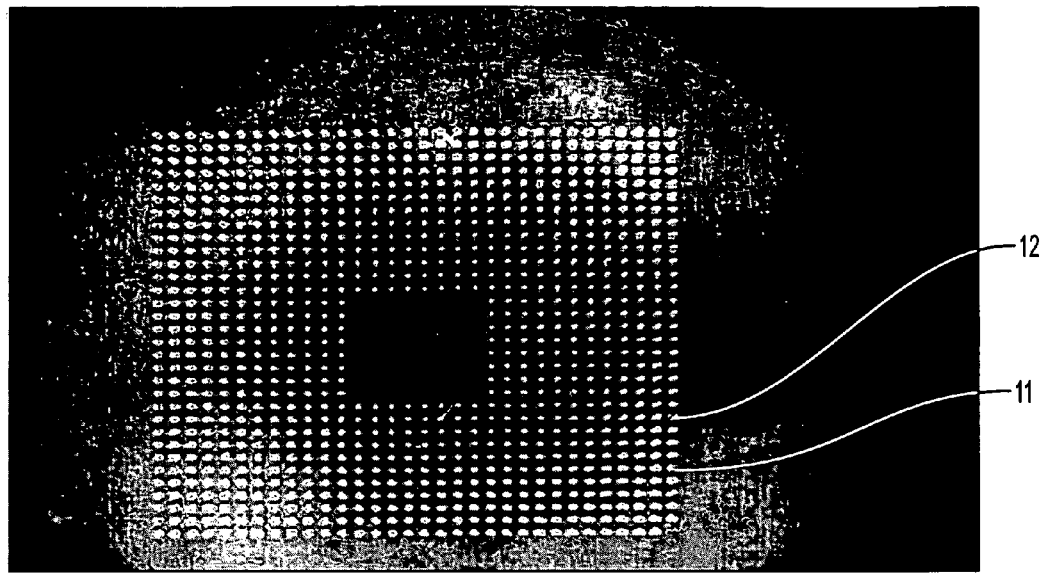
FIG. 7(a) is an image of a pin grid array illuminated with high-angle lighting.
Figure 7B:
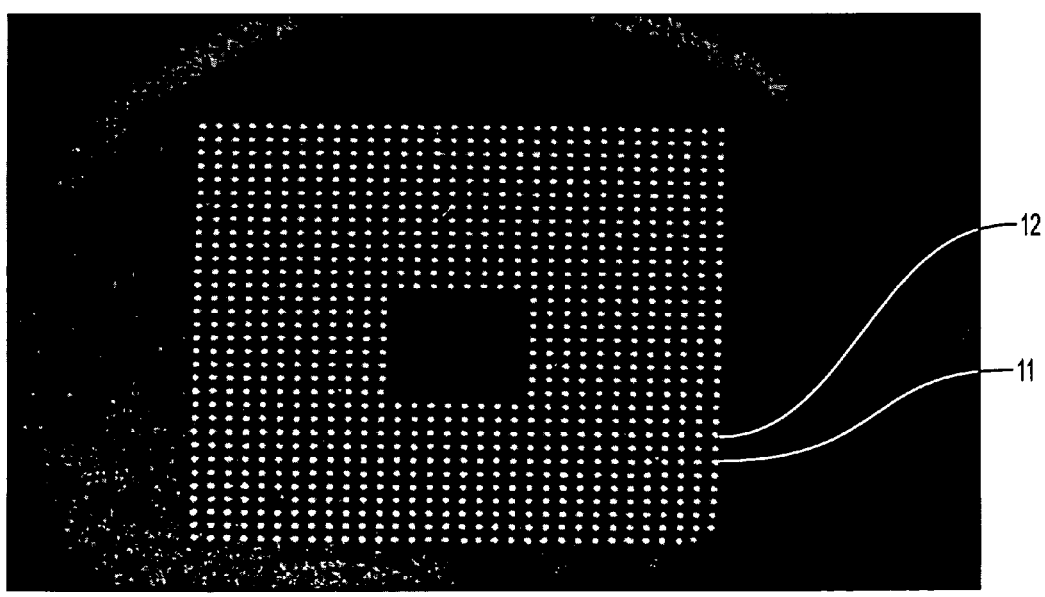
FIG. 7(b) is an image of the masked pin grid array in FIG. 7(a) illuminated with dark-field, low-angle lighting in accordance with an embodiment of the invention.

FIGS. 7(a) and 7(b) illustrate the advantages obtained using dark-field, low-angle illumination versus high-angle lighting. FIG. 7(a) is an image of a masked PGA 15 illuminated with high-angle lighting. In contrast, FIG. 7(b) is an image of a masked PGA 15 illuminated with low-angle lighting. As shown in FIG. 7(b), the pin tips are clearly identifiable and distinguishable from other parts of the PGA 15. Further, the pin base 12 is very dark while the pin tip 11 is clearly distinct and visible. This contrast allows the PGA system 1 to detect the condition of pins on the PGA 15 accurately. Thus, the combination of the pin base mask 30 and the dark-field low-angle lighting 40 produce a definitive image that can be easily processed by an image processing algorithm.

Figure 8A:
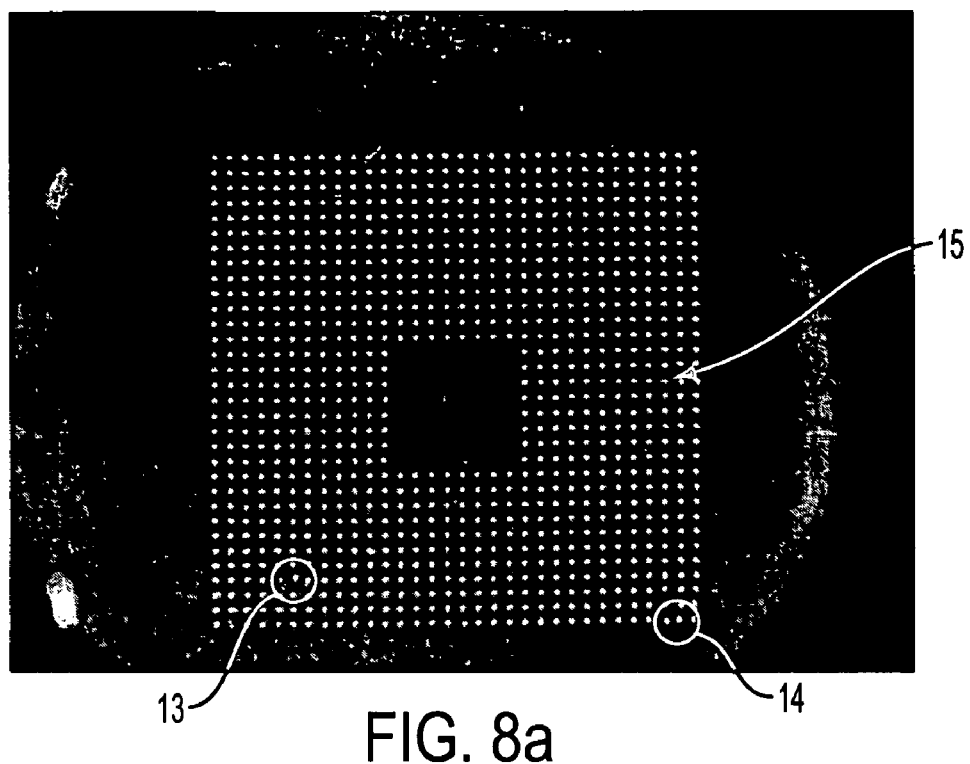
FIG. 8(a) shows an image of a masked pin grid array illuminated with mid-angle lighting.
Figure 8B:
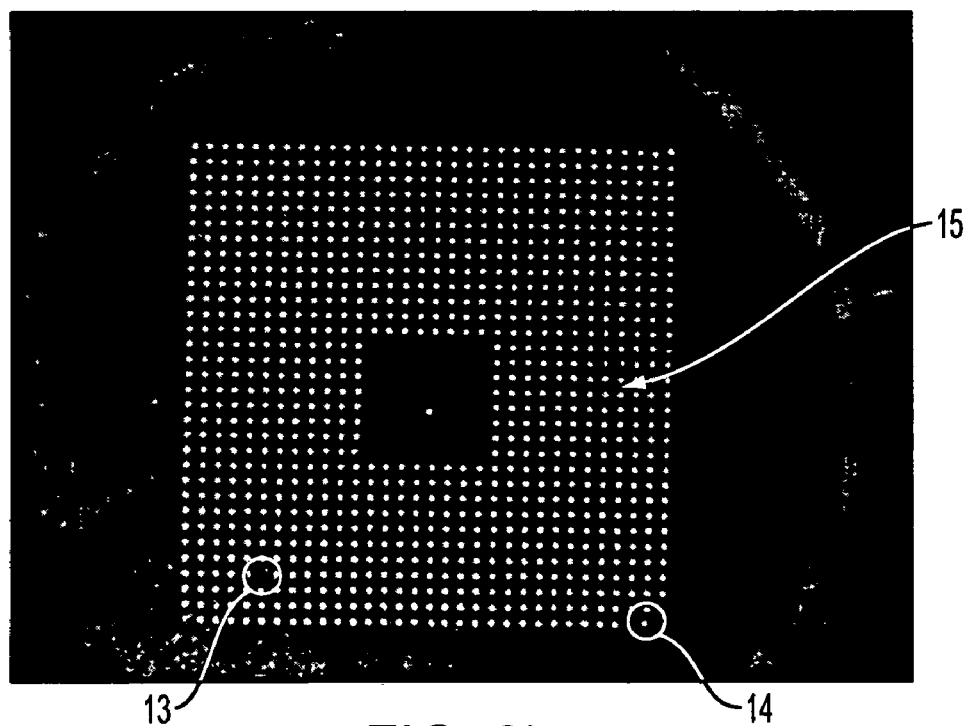
FIG. 8(b) shows an image of a masked pin grid array illuminated with dark-field, low-angle lighting in accordance with an embodiment of the invention.

FIGS. 8(a) and 8(b) are images of the same masked PGA 15 under inspection. FIG. 8(a) is an image captured under mid-angle lighting. FIG. 8(b) is an image captured under dark-field, low-angle lighting. As shown, the PGA 15 has a bent pin 13 on its lower left portion and a severely bent pin 14 on its lower right portion. Comparing FIGS. 8(a) and 8(b), the bent pins 13, 14 are more visible in the image of FIG. 8(b), which was captured under dark-field, low-angle lighting.

As shown in FIG. 2(a), the system further comprises a processor 90 operatively coupled to the camera 50. The processor 90 is configured to execute an algorithm to detect defects in the pins. For example, a least mean square best-fitting algorithm as known in the art may be employed. The least mean square best-fitting algorithm executed by the processor 90 provides for effective pin grid array detection. Specifically, the least mean square best-fitting algorithm uses the pixel data captured by the camera 50 of the IC device 10 under inspection and "fits" this data into a predefined ideal data set.

Further, the processor 90 is also configured to perform blob analysis on images captured by the camera 50. A blob ("binary large object") is an area of adjacent pixels that have the same logical state. Blob analysis can detect blobs in an image and make selected measurements on those blobs. Blob analysis is an efficient algorithm for finding blobs with specific characteristics. Further, blob analysis provides the system with an abundance of statistical information including the size, number and location of blob regions. In the present invention, applying blob analysis to a clearly defined image yields information that enables the PGA inspection system 1 to detect physical defects on the surface of the PGA 15, including determining which pins are bent, misplaced or missing. In the alternative, other known algorithms (such as ball grid array algorithms) may be used by the system.

According to another embodiment of the invention, a controller 70 regulates the light intensity, light levels and distributions of the lighting system 40. Preferably, the controller 70 is comprised of multiple channel light controllers that can be controlled by software. A user may specify or edit the lighting preferences of the PGA system 1 using the controller 70. The electric current of each channel may be set in the range of 0 to 500 mA. In addition, a cooling system 80 is employed to regulate the temperature of the PGA inspection system 1.

Figure 9:
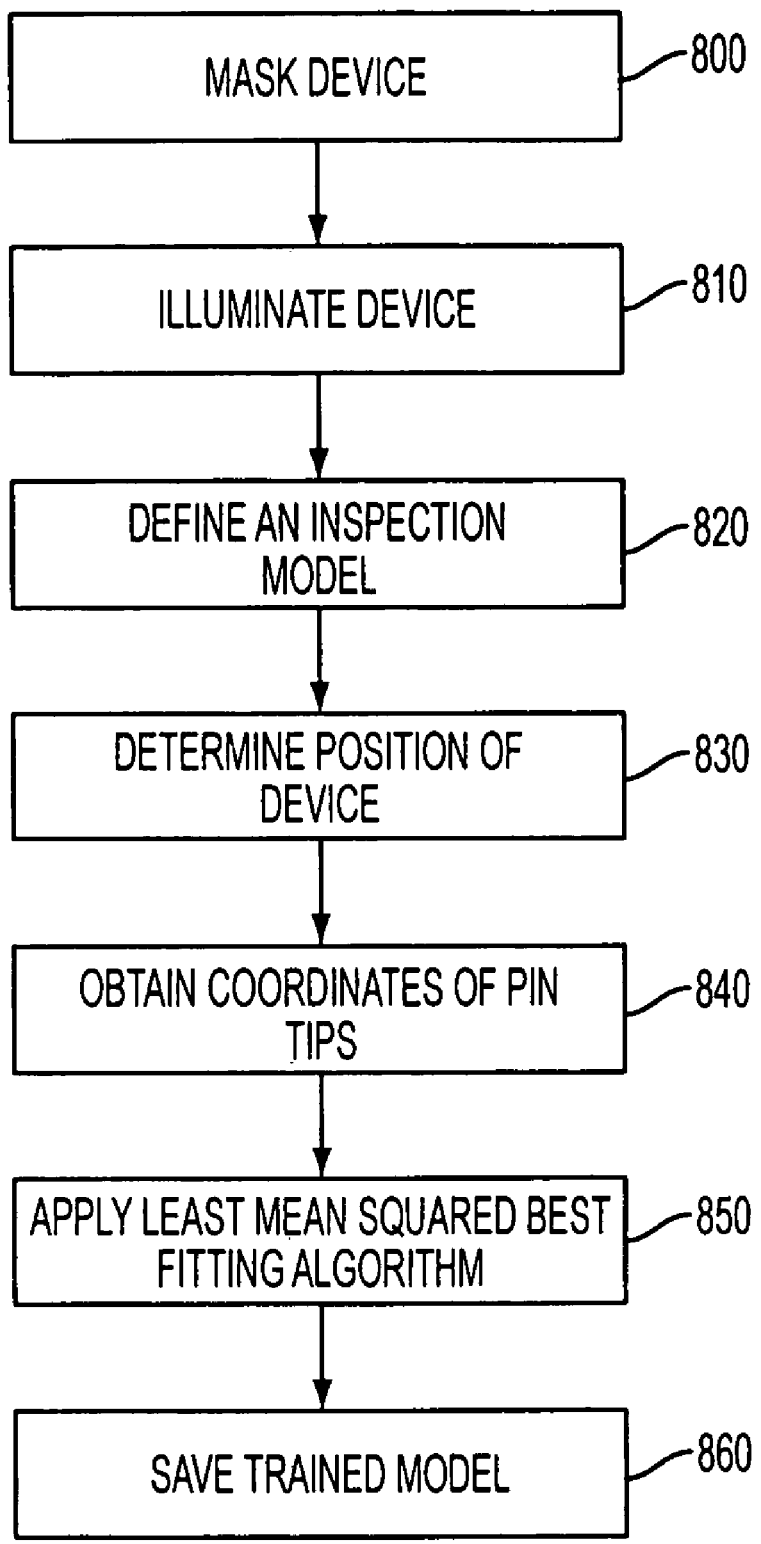
FIG. 9 is a flowchart of a training process for a PGA inspection system according to an embodiment of the invention.

A method for training a PGA system 1 and detecting defects on the PGA 15 of an IC device 10 will now be explained. Again, it should be understood that these methods are illustrative of one embodiment of the invention and that other specific methods are possible. FIG. 9 is a flowchart illustrating a method for training the PGA inspection system 1. As shown in FIG. 9, first, the pin base mask 30 is applied to an IC device (step 800). Next, the lighting system 40 illuminates the masked device (step 810). An inspection model is then defined (step 820). During this step, a user defines the number of rows and columns of pins on the IC devices 10 to be inspected as well as the areas of interest on the PGA 15 of the IC device 10 to be inspected. Further, other specifications such as positional characteristics of the IC device 10 are determined.

Next, the PGA system 1, using the camera 50, determines the accurate position of the IC device 10 (step 830). According to this particular embodiment of the invention, the PGA inspection system 1 employs a normalized cross correlation algorithm. A normalized cross correlation algorithm is a common algorithm used in image processing to detect specific features on a given image. Here, a normalized cross correlation algorithm uses the position information specified in the model definition step 820 to determine position information for the IC device 10. In step 840, the system determines the coordinates of the pin tips 11 of the PGA 15. Next, the system applies a least mean squared best-fitting algorithm to fit the obtained pixel data into the computed ideal data (step 850). It should be understood that other algorithms may also be used to accomplish the same result. Once the model is correctly defined and tested, it may be saved for later use (step 860). Generally, this step must only be completed once for each type of IC device 10.

Figure 10:
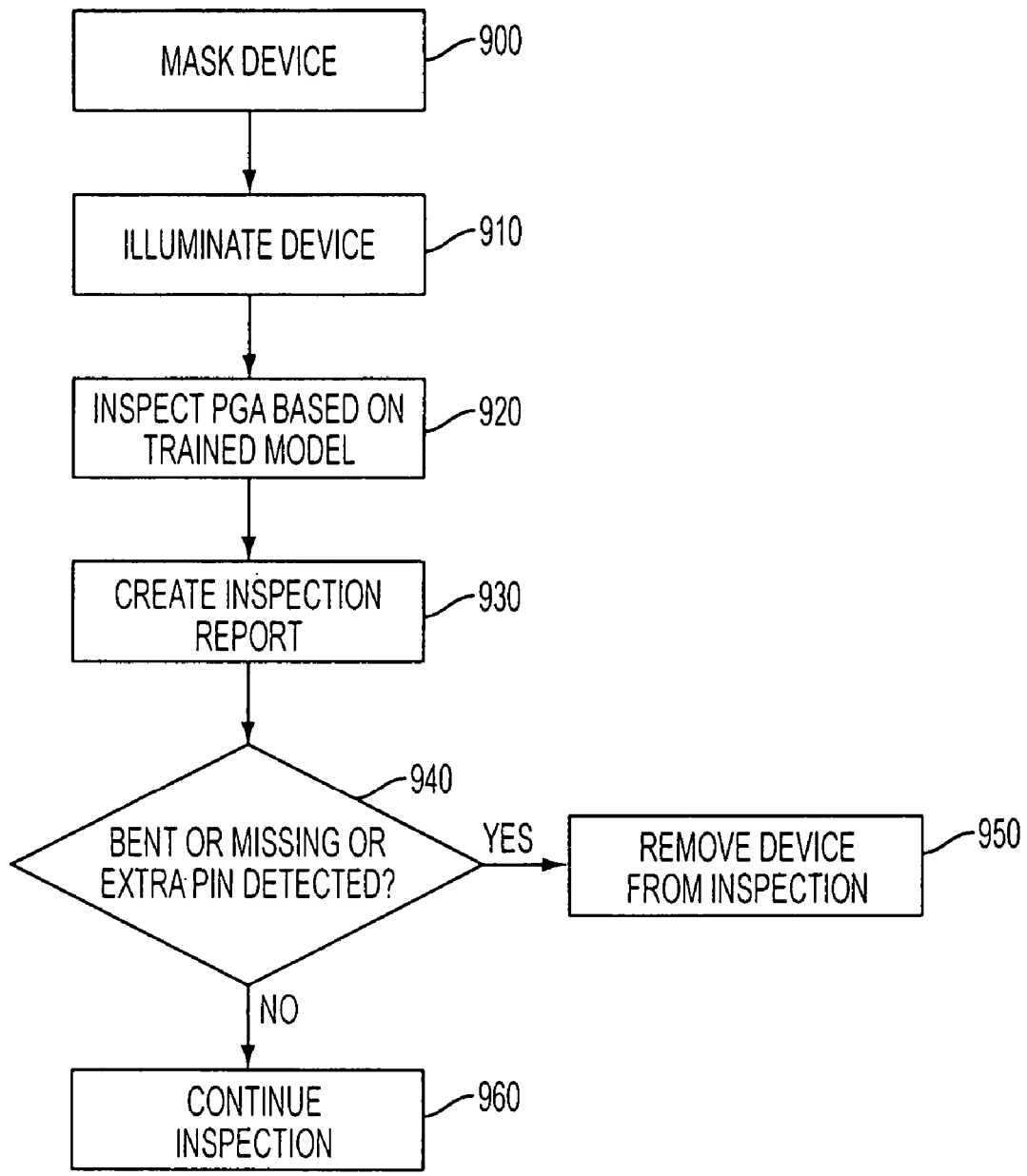
FIG. 10 is a flowchart of a PGA inspection process in accordance with an embodiment of the invention.

FIG. 10 is a flowchart illustrating a method for inspecting a PGA 15 on an IC device 10 using a PGA inspection system 1. First, the IC device 10 under inspection is inserted into the mask 30(step 900). Next, the IC device 10 is illuminated using dark-field, low-angle lighting (step 910). Using the dark-field, low-angle lighting, the IC device 10 is inspected (step 920) for bent, missing or extra pins based on the trained model obtained in step 860. According to this embodiment of the invention, a blob-detection algorithm is then applied to the image captured under dark-field, low-angle lighting to discover the bent, missing or extra pins. According to one embodiment of the invention, a predefined user tolerance is used to identify bent pins. If a pin is bent greater than a predefined threshold value then the PGA system 1 flags that pin as bent.

Next, the PGA inspection system 1 creates a report (step 930) including the details of the inspection. These details may include the number of bent or missing pins, the specific pin or pins that are bent the most and other specific pin information. Finally, as shown in step 940, if a bent, missing or extra pin is detected on the PGA 15, the IC device 10 is removed by the pick and place handler for repair (step 950). If no physical defect is detected, the IC device is moved to the next phase of inspection (step 960).

According to certain aspects of the invention, certain advantages are realized. For example, the present system costs less to implement than currently known systems. In addition, the system can be implemented on various types of handler systems. Furthermore, the system of the present invention is capable of providing more detailed information about a pin grid array than current systems.

Although the present invention has been described in reference to a particular embodiment, various other embodiments and modifications will be apparent to those skilled in the art. It is therefore intended that the foregoing description of a preferred embodiment be considered as exemplary only.

What is claimed is:

1. A pin grid array integrated circuit (IC) device inspection system for a test handler, the pin grid array IC device inspection system comprising:
    a pin base mask having a plurality of pin holes configured to receive a plurality of pins of a pin grid array IC device to be inspected, each of said plurality of pins being disposed on a surface of said device and having a base portion and a lead portion;
    a dark-field, low-angle lighting system for illuminating the pins of the pin grid array as the pins of the pin grid array IC device are received in the pin base mask, wherein a shadow is created on the base portion of the pins as the lead portion is illuminated;
    a camera configured to image the illuminated lead portion of the pins of the IC device; and
    a processor coupled to the camera, configured to analyze images captured by the camera to detect defects in the pin grid array.

2. A pin grid array IC device inspection system for a test handler according to claim 1, wherein an optical axis of the camera is perpendicular to the surface of the pin grid array IC device on which said pins are disposed.

3. A pin grid array IC device inspection system for a test handler according to claim 1, wherein the dark-field, low-angle lighting system emits light uniformly across the pin grid array.

4. A pin grid array IC device inspection system for a test handler according to claim 1, wherein the light emitted by the dark-field, low-angle lighting system has an angle of approximately zero degrees relative to the surface of the pin grid array IC device on which said pins are disposed.

5. A pin grid array IC device inspection system for a test handler according to claim 1, wherein the light emitted by the dark-field, low-angle lighting system has an angle in the range of approximately zero to ten degrees relative to the surface of the pin grid array IC device on which said pins are disposed.

6. A pin grid array integrated circuit (IC) device inspection system for a test handler, the pin grid array IC device inspection system comprising:
    a pin base mask having a plurality of pin holes configured to receive a plurality of pins on a surface of a pin grid array IC device to be inspected;
    a dark-field, low-angle lighting system for illuminating the pins the pin grid array wherein the dark-field, low-angle lighting system is positioned in proximity to the pin base mask;
    a camera configured to image the illuminated pins of the IC device;
    a processor coupled to the camera, configured to analyze images captured by the camera to detect defects in the pin grid array;
    a controller for controlling the dark-field low-angle lighting system; and
    a cooling system operatively coupled to the low-angle lighting system for regulating the temperature of the dark-field low-angle lighting system.

7. A pin grid array IC device inspection system for a test handler according to claim 1, wherein the dark-field low-angle lighting system is comprised of at least one LED array.

8. A pin grid array IC device inspection system for a test handler according to claim 1, wherein the pin base mask has a plurality of pinholes that are chamfered so as to receive the plurality of pins of the pin grid array on an input side of the mask.

9. A pin grid array IC device inspection system for a test handler according to claim 1, wherein the processor is configured to determine a position of the pins using a least mean square best-fitting algorithm on the images captured by the camera.

10. A pin grid array IC device inspection system for a test handler according to claim 1, wherein the processor is configured to detect a defect on the pin grid array using a blob analysis algorithm on an image of the pin grid array captured by the camera.

11. A pin grid array IC device inspection system for a test handler according to claim 1, further comprising:
    a controller for controlling the dark-field low-angle lighting system; and
    a cooling system operatively coupled to the low-angle lighting system for regulating the temperature of the dark-field low-angle lighting system.

12. A pin grid array IC device inspection system for a test handler according to claim 6, wherein an optical axis of the camera is perpendicular to the surface of the pin grid array IC device on which said pins are disposed.

13. A pin grid array IC device inspection system for a test handler according to claim 6, wherein the dark-field, low-angle lighting system emits light uniformly across the pin grid array.

14. A pin grid array IC device inspection system for a test handler according to claim 6, wherein the light emitted by the dark-field, low-angle lighting system has an angle of approximately zero degrees relative to the surface of the pin grid array IC device on which said pins are disposed.

15. A pin grid array IC device inspection system for a test handler according to claim 6, wherein the light emitted by the dark-field, low-angle lighting system has an angle in the range of approximately zero to ten degrees relative to the surface of the pin grid array IC device on which said pins are disposed.

16. A pin grid array IC device inspection system for a test handler according to claim 6, wherein the pin base mask has a plurality of pinholes that are chamfered so as to receive the plurality of pins of the pin grid array on an input side of the mask.

17. A pin grid IC device array inspection system for a test handler according to claim 6, wherein the processor is configured to determine a position of the pins using a least mean square best-fitting algorithm on the images captured by the camera.

18. A pin grid IC device array inspection system for a test handler according to claim 6, wherein the processor is configured to detect a defect on the pin grid array using a blob analysis algorithm on an image of the pin grid array captured by the camera.

19. A pin grid array IC device inspection system for a test handler according to claim 1, wherein said processor is configured to create an inspection report specifying the condition of each pin on the pin grid array of the IC device.

20. A pin grid array IC device inspection system for a test handler according to claim 19, wherein the condition of each pin on the pin grid array of the IC device includes whether the pin is bent.

21. A pin grid array IC device inspection system for a test handler according to claim 19, wherein the condition of each pin on the pin grid array of the IC device includes whether the pin is missing.

22. A pin grid array IC device inspection system for a test handler according to claim 6, wherein said processor is configured to create an inspection report specifying the condition of each pin on the pin grid array of the IC device.

23. A pin grid array IC device inspection system for a test handler according to claim 22, wherein the condition of each pin on the pin grid array of the IC device includes whether the pin is bent.

24. A pin grid array IC device inspection system for a test handler according to claim 22, wherein the condition of each pin on the pin grid array of the IC device includes whether the pin is missing.

* * * * *